United States Patent
Macan et al.

(10) Patent No.: US 8,968,511 B2
(45) Date of Patent: Mar. 3, 2015

(54) MEDICAL DEVICE AND TECHNIQUE FOR USING THE SAME

(71) Applicant: Covidien LP, Mansfield, MA (US)

(72) Inventors: Aaron D. Macan, Loveland, CO (US); Dhairya K. Mehta, Woodland Hills, CA (US); Sarah L. Hayman, Boulder, CO (US); Jon W. Neal, Parker, CO (US); Mark R. Behlmaier, Erie, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/744,872

(22) Filed: Jan. 18, 2013

(65) Prior Publication Data

US 2013/0126087 A1 May 23, 2013

Related U.S. Application Data

(63) Continuation of application No. 12/362,214, filed on Jan. 29, 2009, now Pat. No. 8,381,730.

(51) Int. Cl.
*A61M 16/04* (2006.01)
*B29D 23/00* (2006.01)
(Continued)

(52) U.S. Cl.
CPC ............... *B29D 23/00* (2013.01); *A61M 16/04* (2013.01); *B29C 49/52* (2013.01); *B29C 65/02* (2013.01); *B29C 65/7802* (2013.01); *B29C 66/1122* (2013.01); *B29C 66/53241* (2013.01); *A61M 16/0434* (2013.01); *A61M 2205/32* (2013.01); *A61M 2205/6036* (2013.01); *A61M 2205/6063* (2013.01); *B29C 49/04* (2013.01); *B29C 49/48* (2013.01); *B29C 65/7817* (2013.01);
(Continued)

(58) Field of Classification Search
CPC ..... A61M 31/00; A61M 16/00; A61M 16/04; A61M 29/00; A61M 25/00
USPC ........ 128/207.15, 207.14; 604/96.01, 103.01; 156/293
See application file for complete search history.

(56) References Cited

U.S. PATENT DOCUMENTS

| | | | |
|---|---|---|---|
| 3,565,079 A | 2/1971 | Jackson | |
| 4,091,816 A | 5/1978 | Elam | |

(Continued)

FOREIGN PATENT DOCUMENTS

WO        2008011373        1/2008

OTHER PUBLICATIONS

Dullenkopf, A. et al., Air Leakage Around Endotracheal Tube Cuffs, European Journal of Anaesthesiology, Dec. 2004, pp. 448-453, Issue 21.

(Continued)

*Primary Examiner* — Jeff Aftergut
*Assistant Examiner* — Jaeyun Lee
(74) *Attorney, Agent, or Firm* — Fletcher Yoder PC

(57) ABSTRACT

An inflatable balloon cuff may be adapted to seal a patient's trachea when associated with an endotracheal tube. These cuffs may include indicia that facilitate attachment of the cuff relative to the tube to reduce manufacturing variability for such characteristics as rotational and length alignment. Such indicia may include protrusions that are formed in the wall of the cuff collars or may include visual indicators, e.g., colorimetric or shape-wise indicators. Cuffs with improved attachment relative to the tube may have increased sealing performance.

9 Claims, 6 Drawing Sheets

(51) Int. Cl.

| | |
|---|---|
| *B29C 49/52* | (2006.01) |
| *B29C 65/02* | (2006.01) |
| *B29C 65/78* | (2006.01) |
| *B29C 65/00* | (2006.01) |
| B29C 49/04 | (2006.01) |
| B29C 49/48 | (2006.01) |
| B29C 49/20 | (2006.01) |
| B29K 75/00 | (2006.01) |
| B29L 31/00 | (2006.01) |

(52) U.S. Cl.
CPC . *B29C2049/2017* (2013.01); *B29C 2049/2069* (2013.01); *B29C 2049/4882* (2013.01); *B29K 2075/00* (2013.01); *B29L 2031/7542* (2013.01)
USPC ............... 156/293; 604/103.01; 604/96.01; 128/207.15; 128/207.14

(56) References Cited

U.S. PATENT DOCUMENTS

| | | | |
|---|---|---|---|
| 4,141,364 | A | 2/1979 | Schultze |
| 4,231,365 | A | 11/1980 | Scarberry |
| 4,235,239 | A | 11/1980 | Elam |
| 4,341,210 | A | 7/1982 | Elam |
| 4,423,725 | A | 1/1984 | Baran et al. |
| 4,976,261 | A | 12/1990 | Gluck et al. |
| 5,033,466 | A | 7/1991 | Weymuller, Jr. |
| 5,315,992 | A | 5/1994 | Dalton |
| 5,437,290 | A | 8/1995 | Bolger |
| 5,693,014 | A | 12/1997 | Abele et al. |
| 5,772,629 | A | 6/1998 | Kaplan |
| 6,048,332 | A | 4/2000 | Duffy et al. |
| 6,736,841 | B2 | 5/2004 | Musbach et al. |
| 6,786,889 | B1 | 9/2004 | Musbach et al. |
| 6,802,317 | B2 | 10/2004 | Gobel |
| 6,889,693 | B2 | 5/2005 | Hipolito et al. |
| 6,953,431 | B2 | 10/2005 | Brothel |
| 7,156,827 | B2 | 1/2007 | McNary et al. |
| 7,195,612 | B2 | 3/2007 | van Sloten et al. |
| 7,478,636 | B2 | 1/2009 | Madsen et al. |
| 7,921,847 | B2 | 4/2011 | Totz |
| 2004/0116898 | A1 | 6/2004 | Hawk |
| 2004/0267195 | A1 | 12/2004 | Currlin |
| 2007/0137652 | A1 | 6/2007 | Qureshi et al. |
| 2008/0029100 | A1 | 2/2008 | Glassenberg et al. |
| 2008/0228138 | A1 | 9/2008 | van Sloten et al. |
| 2008/0230070 | A1 | 9/2008 | Gregorian |
| 2010/0006103 | A1 | 1/2010 | McGinnis et al. |

OTHER PUBLICATIONS

Park, Sang-Hyun MD et al., The Influence of Head and Neck Position on the Oropharyngeal Leak Pressure and Cuff Position of Three Supraglottic Airway Devices, Anesthesia and Analgesia, Jan. 2009, pp. 112-117, vol. 108, No. 1.
Cohen Endobronchial Blocker, Cook Medical, http://www.cookmedical.com/cc/dataSheet.do?id=3989, Mar. 2010, pp. 1-2.
EndoFlex, Endotracheal Tubes, Medline, pp. 4-5.
Microcuff Endotracheal Tube and Pediatric ETT, Kimberly-Clark, (2010) pp. 1-18.
Rusch, Teleflex Medical, http://www.teleflexmedical.com/prod_rusch.php, (2009) pp. 1-9.
Sheridan PED—Soft Uncuffed Endotracheal Tubes, Teleflex Medical—Hudson RCI, (Apr. 2010) pp. 1-3.
Sheridan Performed Endotracheal Tubes, Teleflex Medical—Hudson RCI, (Apr. 2010) pp. 1-3.
Sheridan Sher-I-Bronch Endobrochial Tubes, Teleflex Medical—Hudson RCI, (Apr. 2010) pp. 1-4.
Tracoe Comfort medical GmbH, http://www.tracoe.com/products/6/comfort/html, (Apr. 2010) pp. 1-4.

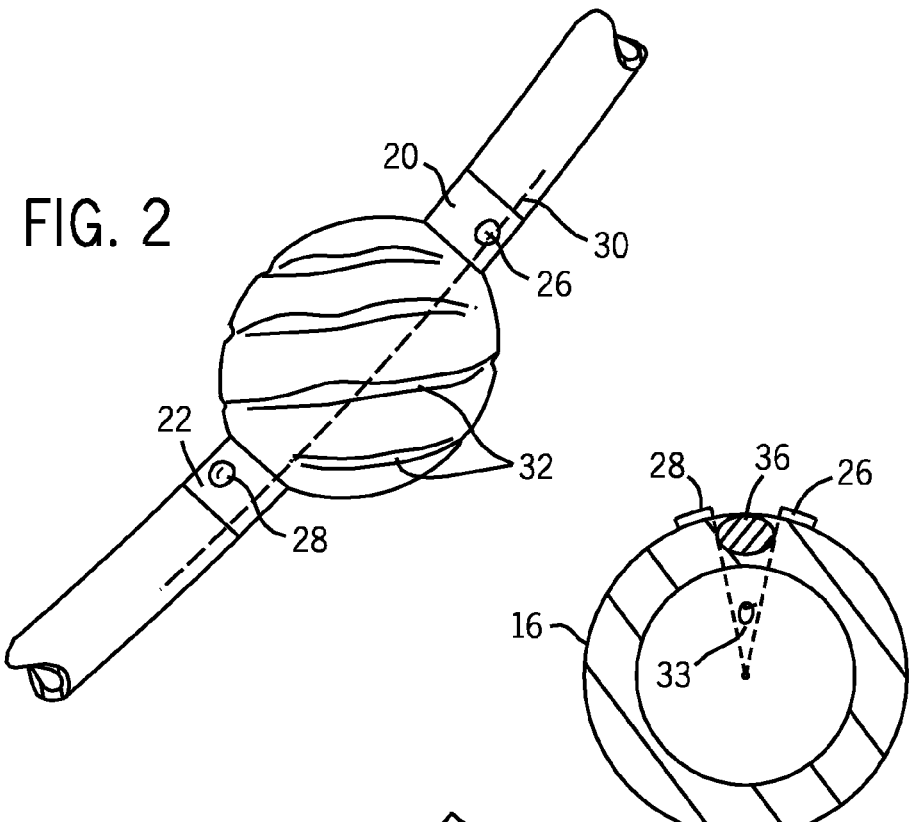
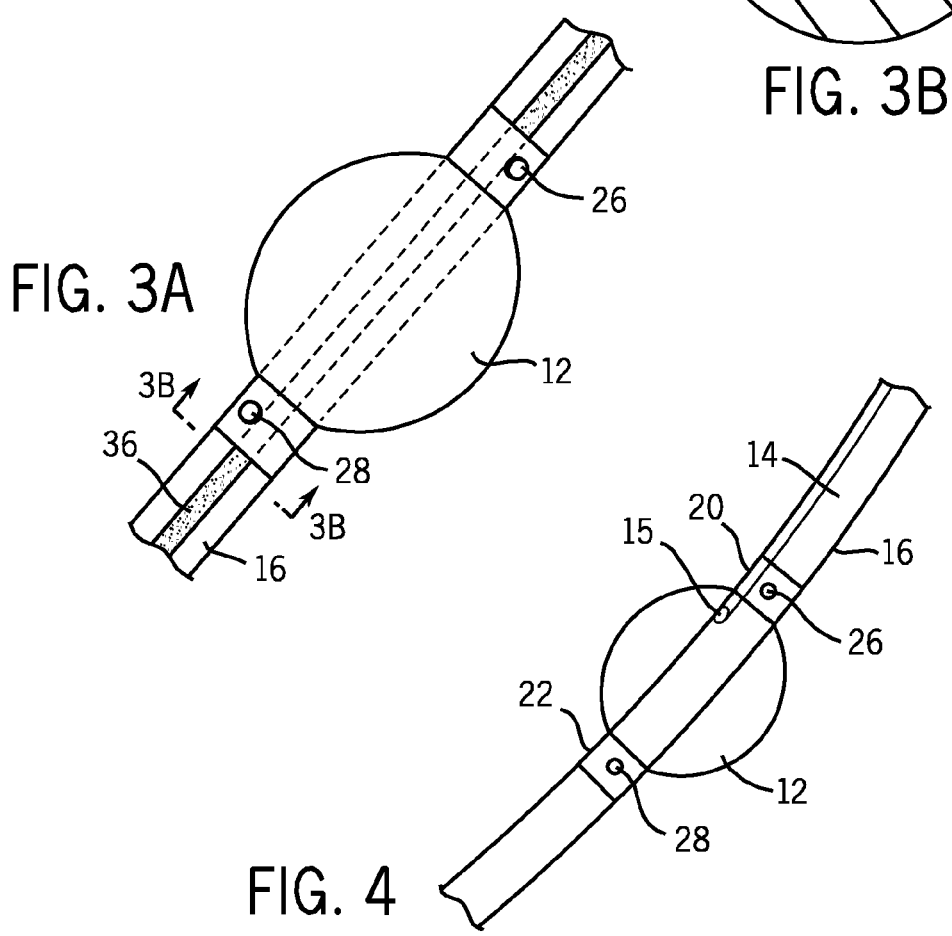

MEDICAL DEVICE AND TECHNIQUE FOR USING THE SAME

CROSS-REFERENCE TO RELATED APPLICATION

This application is a continuation of U.S. application Ser. No. 12/362,214, filed on Jan. 29, 2009, the disclosure of which is hereby incorporated by reference in its entirety for all purposes.

BACKGROUND

The present disclosure relates to medical devices, and more particularly, to airway products, such as tracheal tubes and cuffs.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, a tube or other medical device may be used to control the flow of air, food, fluids, or other substances into the patient. For example, medical devices such as tracheal tubes may be used to control the flow of one or more substances into or out of a patient. In many instances it is desirable to provide a seal between the outside of the tube or device and the interior of the passage in which the tube or device is inserted. In this way, substances can only flow through the passage via the tube or other medical device, allowing a medical practitioner to maintain control over the type and amount of substances flowing into and out of the patient.

For example, tracheal tubes may be used to control the flow of air or other gases through a patient's trachea. Such tracheal tubes may include endotracheal (ET) tubes, tracheostomy tubes, or transtracheal tubes. To seal these types of tracheal tubes, an inflatable cuff may be associated with these tubes. When inflated, the cuff generally expands into the surrounding trachea to seal the tracheal passage around the tube.

Typically, cuffs are attached to tracheal tubes via an adhesive or by a heat bonding process. Because the cuffs are generally made from a relatively thin and flexible material, the cuffs may be distorted during the attachment process. For example, the cuffs may be twisted along the axis of the tube and attached to the tube in a twisted position. A twisted cuff may have an irregular inflation shape that may lead to decreased sealing efficiency or an increased incidence of wrinkling, whereby the wrinkles may create a "corkscrew" effect. In addition, a cuff may be compressed or stretched along the axis of the tube before being sealed to the tube, which may lead to a cuff that is improperly placed relative to the tube and that may have decreased sealing performance. For example, a relatively stretched cuff may have more pronounced wrinkles, which may serve as leak paths into the lungs for secretions that form at the top of the cuff. A relatively compressed cuff may have too much cuff material which will form many wrinkles when inflated and, therefore, may provide a decreased seal quality and also increases the risk that secretions will leak past the cuff into the lungs. Such secretions often contain micro-organisms that, upon aspiration by the patient, can result in complications. There remains a need in the art for an improved cuff and means of mounting the cuff to a tracheal tube that may enhance sealing performance and inhibit aspiration of secretions.

BRIEF DESCRIPTION OF THE DRAWINGS

Advantages of the disclosure may become apparent upon reading the following detailed description and upon reference to the drawings in which:

FIG. 2 illustrates an exemplary balloon cuff in a twisted conformation prior to being correctly adhered to a tube according to embodiments;

FIG. 3A illustrates the balloon cuff of FIG. 2 with the indicators aligned along an X-ray line on the tube;

FIG. 3B is a cross-sectional view of the cuff and tube of FIG. 3A;

FIG. 4 illustrates an exemplary balloon cuff in a compressed conformation prior to being correctly adhered to a conduit according to embodiments;

DETAILED DESCRIPTION

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

It is desirable to provide a medical balloon, such as an endotracheal cuff or other medical balloon, that may efficiently seal the passage in which the cuff is inserted so that mechanical ventilation can be used to introduce air, oxygen, other gases, or medications into the lungs. Provided herein are balloon cuffs with features that allow an operator or automatic quality system to align a cuff against a tracheal tube to minimize stretching, compressing, twisting, or out of specification axial placement of the cuff relative to the tube. Such cuffs may include raised protrusions or other markers on the wall of the cuff that may serve as alignment indicators for aligning the cuff against the tube.

Medical cuffs as provided herein may be used in conjunction with any suitable medical device. Preferably, the medical cuffs as provided herein may be used in conjunction with an endotracheal tube, a tracheostomy tube, a circuit, an airway accessory, a connector, an adapter, a filter, a humidifier, a nebulizer, or a prosthetic. Medical cuffs as provided herein may include those as disclosed in "MEDICAL DEVICE AND TECHNIQUE FOR USING THE SAME," by Macan, et al., filed on Jan. 29, 2009, which is incorporated by reference herein in its entirety for all purposes.

Figure 1:
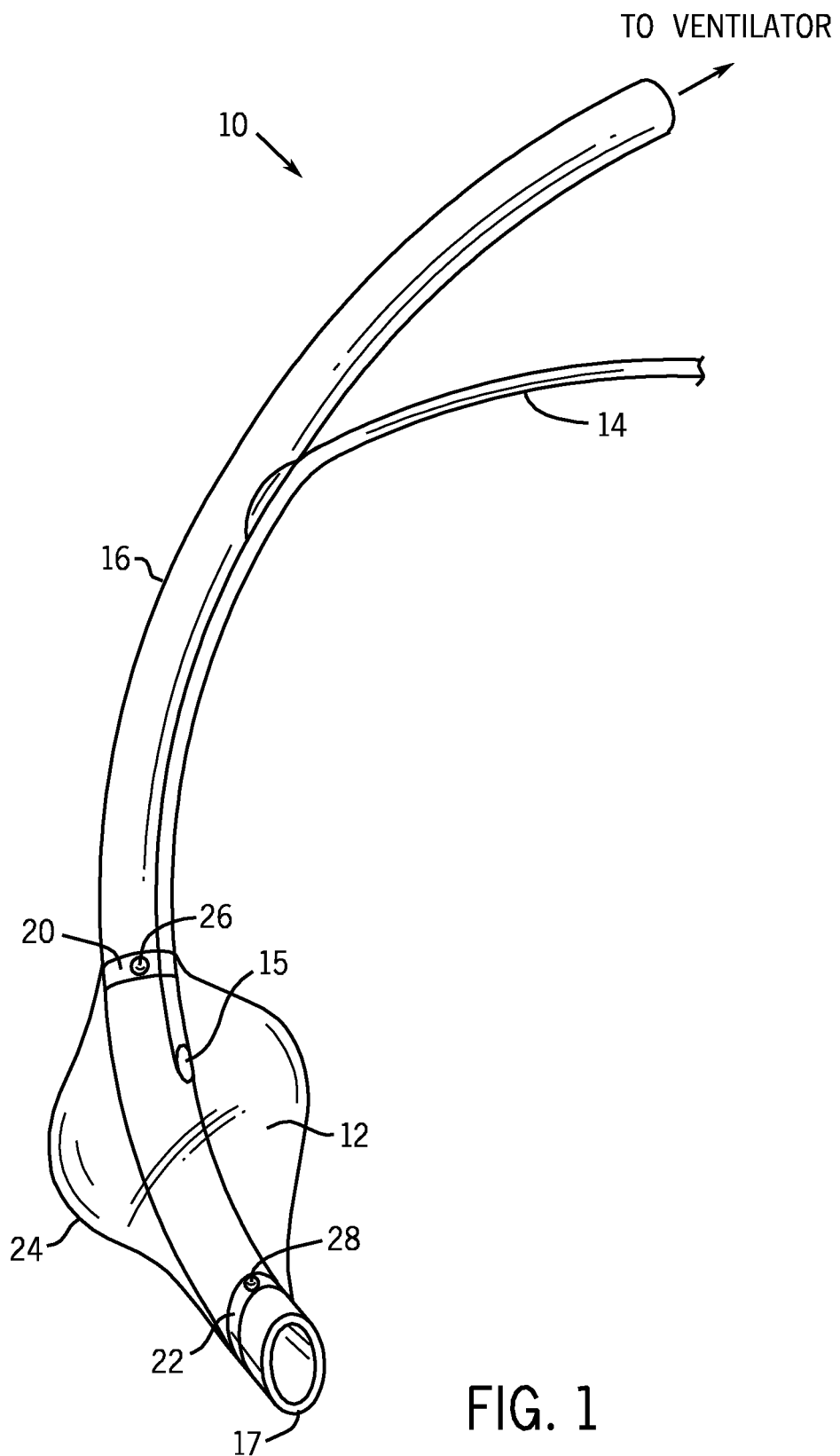
FIG. 1 illustrates an endotracheal tube with an inflatable balloon cuff with indicators on distal and proximal collar regions in the cuff in accordance with embodiments.

Provided herein is an exemplary cuffed endotracheal tube 10, depicted in FIG. 1. The cuffed endotracheal tube 10 includes an inflatable medical cuff 12 that may be inflated to form a seal against the trachea wall. The medical cuff 12 is disposed on an endotracheal tube 16, which is a conduit that is suitably sized and shaped to be inserted into a patient and allow the passage of air through the airway path of the endotracheal tube 16. Typically, the cuff is disposed, adhesively or otherwise, towards the distal end 17 of the endotracheal tube 16. The medical cuff 12 may, for example, be inflated and deflated via a lumen 14 in communication with the medical cuff 12, typically through a hole or notch 15 in the endotracheal tube 16. The medical cuff 12 includes a proximal collar region 20 and a distal collar region 22 formed in the cuff walls and sized to accommodate the endotracheal tube 16. The proximal collar 20, located closer to the "machine end" of the tube 16, and a distal collar 22, located closer to the "patient end" of the tube 16, are typically used to mount the cuff 12 to the tube 16. The collar regions 20 and 22 flank an inflatable region 24, which is in fluid communication with lumen 14. In embodiments, the cut edges of the cuff 12 may be used to position the cuff 12 relative to other features on the tube (e.g., tube tip, Murphy eye).

The medical cuff 12 may be formed from materials having suitable mechanical properties (such as puncture resistance, pin hole resistance, tensile strength), chemical properties (such as forming a suitable bond to the tube 16), and biocompatibility. In one embodiment, the walls of the inflatable cuff 12 are made of a polyurethane having suitable mechanical and chemical properties. An example of a suitable polyurethane is Dow Pellethane® 2363-90A. In another embodiment, the walls of the inflatable cuff 12 are made of a suitable polyvinyl chloride (PVC). Other suitable materials include polypropylene, polyethylene teraphthalate (PETP), low-density polyethylene (LDPE), silicone, neoprene, polyisoprene, or polyurethane (PU).

The cuff 12 also may include alignment indicia or indicators 26 and 28, which may be indicators of any type, including text, image, ink, chemical, or topographic markers. Further, although only indicia 26 and 28 are shown, it should be understood that any suitable number of alignment indicators may be present. Further, each indicator, e.g., 26 and/or 28, may include multiple markings or members. For example, an alignment indicator may include a group of dots. As shown, indicator 26 and indicator 28 are associated with the proximal collar 26 and the distal collar 28, respectively. In an embodiment, the alignment indicia 26 and 28 may be raised protrusions. The indicia 26 and 28 may be part of the cuff wall material and may be formed in the proximal collar 20 and distal collar 22 regions formed in the cuff wall. Alternatively, the indicia 26 and 28 may be adhesively or otherwise attached to the cuff material after assembly of the cuff 12. The indicia 26 and 28 may be sized and shaped in any suitable configuration that does not substantially prevent the proximal collar region 20 and the distal collar region 22 from adequately sealing to the tube 16. In embodiments, the indicia may be raised relative to the cuff walls at least enough for an operator to feel them with a fingertip, to see them with a naked eye or under magnification (e.g., illuminated magnification), or for a machine to sense them optically or by other modalities. In embodiments, the indicia are raised relative to the proximal collar 20 or distal collar 22 at least about 0.1 mm, at least about 0.125 mm, at least about 0.5 mm, at least about 1 mm, at least about 2 mm, or at least about 3 mm. In addition, the indicia may be raised on the exterior surface of the cuff collars, i.e., the tracheal-facing surface. In addition, the indicia may be raised relative to the interior, i.e., the tube adhesion surface of the cuff collars. In such embodiments, when the cuff 12 is pressed against the tube 16, the raised portions may also be pushed against the tube 16 when the cuff 12 is adhered to the tube 16.

In an embodiment, a colored ink may be used to form all or part of an alignment indicator or to emphasize the features of a protrusion against the cuff 12. In other embodiments, chemical tags may be used to form the alignment indicator. For example, a UV light may be used to visualize alignment indicators that include UV or fluorescent paints.

The alignment indicators (e.g., indicators 26 and 28) may be used to check cuff length and cuff twisting relative to the tube 16. Because the positions of the proximal collar 20 and distal collar 22 regions do not change substantially with the inflation state of the cuff 12, alignment indicators in these regions may be used to check cuff application quality in both inflated and uninflated cuffs. Specifically, because these opening regions 20 and 22 may be substantially adhered to the tube 16, during an inflation spot check the protrusions in these regions maintain close contact with the exterior surface (i.e., tracheal wall-facing surface) of the tube 16. Accordingly, indicators 26 and 28, such as protrusions, may be more easily aligned against markers on the tube 16 than any marker in the inflated region 24, which is generally not in close proximity to the surface of the tube 16.

FIG. 2 shows an exemplary cuff 12 applied to a tube 16 for an inflation spot-check prior to final adhesion of the cuff 12 to the tube 16. As shown, the cuff 12 is twisted, and a proximal indicator 26 and distal indicator 28, depicted as protrusions, are not aligned along an imaginary axis 30 extending through one of the indicators, for example, extending from indicator 26 as shown in FIG. 2, and running along the length of the tube 16. The twisted conformation of the cuff 12 may prevent full inflation of the cuff 12 within the trachea, which may lead to inefficient sealing. In addition, the twisted conformation may increase the formation of wrinkles 32 in the cuff 12, which may in turn increase the availability of leak paths from the top of the cuff into the lungs. Accordingly, the rotation of the cuff 12 relative to the tube 16 may need to be altered prior to adhering the cuff 12. The misalignment of indicators 26 and 28 may be spotted by an operator manually applying the cuff 12 to the tube 16. Alternatively, the quality control may be performed by a machine capable of sensing a thickness in the cuff material or a visual marker at the site of each indicator (e.g., indicators 26 and 28) and either alerting the operator to the misalignment or automatically aligning the indicators along the tube length based on the sensed cuff material thickness. In an embodiment, the indicators may include a marker that may be imaged by a machine to assist in locating the indicators on the cuff 12 prior to alignment. For example, the markers may include color markers, fluorescent markers, or ultraviolet light-visible markers, that, when imaged, may be manually or automatically identified to provide an indication of cuff alignment and/or placement.

In another embodiment, turning to FIG. 3A, the cuff 12 may be aligned relative to the tube 16 by other features on the tube 16. In one embodiment, the feature may be an X-ray line 36 that is marked on the tube 16, for example by a radio opaque color, and runs along the length of tube 16. The X-ray line may serve to provide an indication of the location of the tube 16 during X-ray visualization. In an embodiment, the X-ray line 36 may also provide the manufacturing tolerance for the rotational alignment. For example, the manufacturing tolerance may be that both indicators 26 and 28 must be touching the X-ray line 36. In such embodiments, the effective manufacturing tolerance is the width of the X-ray line 36. For example, in an embodiment, the manufacturing tolerance may be equal to or less than a certain angle offset of the indicators. Such an offset angle 33 may be determined by examining the alignment of indicators 26 and 28 as viewed through a cross-section of the tube 16, as shown in FIG. 3B. In FIG. 3B, indicators 26 and 28 are touching the X-ray line 32 and are, thus, within a manufacturing tolerance. The offset angle 33 may be, in embodiments, equal to or less than 37°, equal to or less than 30°, or equal to or less than 27. In addition, the offset angle 33 tolerance may be different depending on the size or shape of the cuff 12. In other embodiments, the manufacturing tolerance may be indicated on the tube by additional alignment markers. For example, in one embodiment, a dedicated alignment line having a different placement and/or width than the X-ray line 36 may be marked on the tube 16. In an embodiment, the line may be a different color than the X-ray line 36, for example, the X-ray line 36 may be marked in blue while the alignment line may be pink or green.

In addition to rotational alignment, a cuff 12 may be aligned with respect to its length along the tube 16. FIG. 4 illustrates a balloon cuff that is in an incorrect compressed conformation prior to being adhered to a conduit. When applying a typical cuff 12 to the tube 16, an operator may align the proximal collar 20 to a location on the tube 16 directly above notch 15 so that the inflatable region 24 is in fluid communication with the lumen 14. However, the distal collar 22 may then be applied to the tube 16 intuitively by the operator. That is, the operator uses personal experience to guess at a correct cuff length. This may lead to variability in the cuff length based on the experience level of the operator. Accordingly, using this method, a higher number of cuffs 12 may be outside of a cuff length manufacturing tolerance, e.g., about 2.1 inches to about 2.3 inches or about 53 mm to about 58.4 mm, which may lead to waste as these cuffed tubes are discarded at later stages in the manufacturing process. In addition, quality checking procedures may include a direct measurement of cuff length with a ruler, which may be time-consuming and challenging because both the cuff 12 and the tube 16 are relatively transparent and may be difficult to differentiate from one another at the adhesion regions of the cuff 12.

Figure 5:
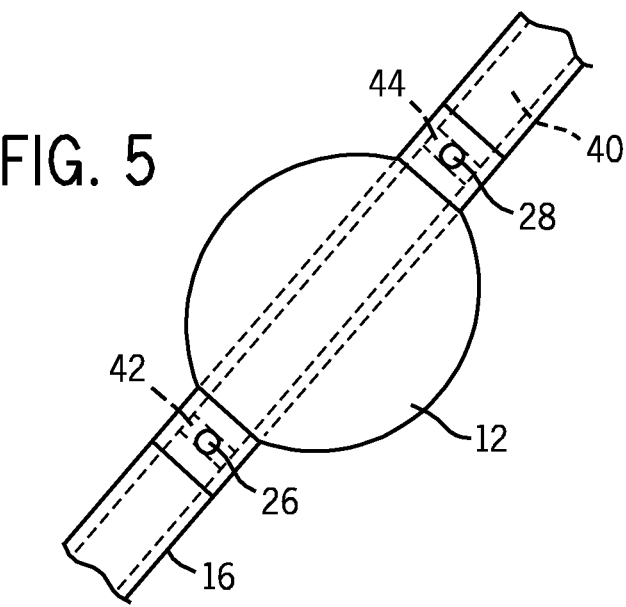
FIG. 5 illustrates an exemplary balloon cuff with indicators being aligned against a mandrel inserted through the interior of the tube according to embodiments.

In embodiments, cuffs 12 as provided may be easily checked for relative length against the tube 16. FIG. 5 illustrates a cuff 12 being checked for length by aligning markers on the cuff 12 with markers on an alignment rod 40 (e.g., a mandrel) inserted through the flow path of tube 16. The rod 40 may include alignment lines 42 and 44 that may be aligned with indicators 26 and 28 as shown. Alignment lines 42 and 44 may be brightly colored to facilitate rapid spot checks of the cuff length. The alignment lines 42 and 44 may be set to reflect the manufacturing cuff length goal, with a tolerance being built into the width of these lines. For example, the tolerance may be met if both indicators 26 and 28 are at least touching their respective lines 42 and 44. In an embodiment, the cuff rotational alignment may be performed simultaneously with the cuff length alignment while the rod 40 is inserted in the tube 16. In embodiments in which the rod 40 is substantially rigid, the slightly curved tube 16 may be straightened upon insertion of the rod 40, which may allow operators to more easily perform fine rotational alignment of indicator 26 with indicator 28 along the length of tube 16. In other embodiments, the cuff length may be verified with a ruler, a caliper, or a go/no-go gauge.

Figure 6:
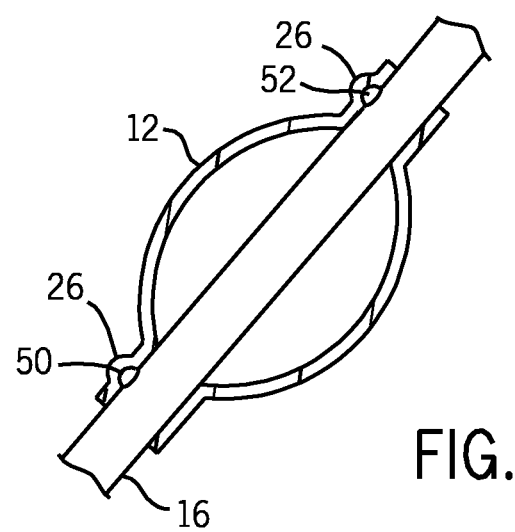
FIG. 6 illustrates an exemplary balloon cuff with indicators being aligned against corresponding protrusions on the tube.

While operators may employ alignment accessories, such as rod 40, in assisting with length alignment of the cuff 12, the tube 16 may, in embodiments, also include indicators or features that may be used to align the cuff 12 with respect to length in addition to rotational alignment (e.g., the X-ray line depicted in FIG. 3). For example, a tube 16 may include indicators that may be aligned with markers on the cuff 12. As shown in FIG. 6, a tube 16 may include proximal protrusion 50 and distal protrusion 52 which may be aligned to proximal indicator 26 and distal indicator 28, shown here as protrusions. Such shaped or visual alignment features on both the tube 16 and the cuff 12 may be aligned by both feel and/or sight by the operator, which may improve the ease and accuracy of the alignment.

Figure 7:
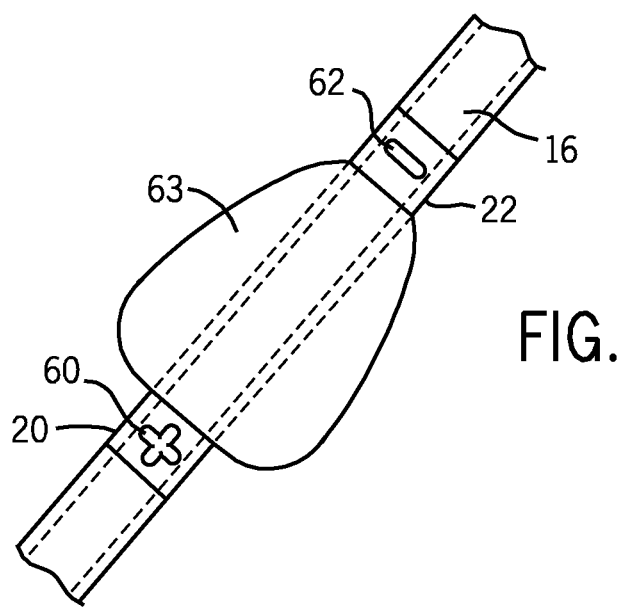
FIG. 7 depicts an embodiment of a balloon cuff with shaped protrusions.

In embodiments, a cuff 12 may be bi-directional, i.e., the cuff 12 may be generally symmetric along an axis perpendicular to an axis through proximal collar 20 and distal collar 22 at the midpoint of the cuff length along the tube 16. In such embodiments, the distal collar 20 may be applied to the proximal adhesion point of the tube and vice versa. However, in certain embodiments, a cuff 12 may be unidirectional and may have a specified orientation along the tube. For example, FIG. 7 depicts an embodiment of an endotracheal tube with a tapered balloon cuff 63 in which the widest diameter is located towards the proximal end of the cuff 63. Because cuffs 12 may be applied to the tube 16 prior to inflation, it may be difficult to determine which end of the tapered cuff 63 is the proximal collar 20 while the cuff 63 is in the uninflated state because the direction of the taper may not be evident when the tapered cuff 63 is uninflated. As provided herein, a tapered cuff 63 may include a proximal marker 60 that is different than a distal marker 62 that may facilitate the application of the proximal collar 20 to the proximal cuff adhesion point of the tube 16. An operator may easily determine in which direction the cuff 63 should be oriented by observing shaped proximal marker 60, which as shown, may be in a "+" shape, versus shaped distal marker 62, which may be in a "−" shape. Any suitable combination of shaped protrusion or colored markers may be used. For example, proximal marker 60 may be green while distal marker 62 may be red and so forth. In other embodiments, a combination of shaped protrusions and colors may be used.

Figure 8:
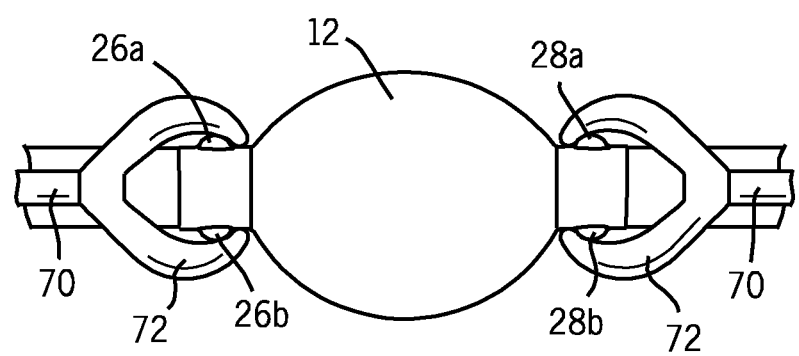
FIG. 8 depicts an embodiment of a balloon cuff with multiple protrusions on the proximal and distal opening regions respectively.

While alignment indicators as provided herein may be used by an operator in manually applying cuffs 12 to tubes 16, it is envisioned that the present embodiments may also be used with automatic alignment as performed by a machine or assembly system. FIG. 8 is an embodiment of a balloon cuff with multiple indicators, depicted as protrusions, on the proximal and distal opening regions 20 and 22, respectively. For example, such an embodiment may be advantageous for use with an assembly machine that may provide attachment arms 70 with pincer grips 72 that may grip the cuff 12 at indicators 26a and 26b on the proximal end of the cuff 12 and at 28a and 28b at the distal end of the cuff 12. The location of the indicators 26a, 26b and 28a, 28b may facilitate proper gripping of the cuff 12 by the assembly machine prior to alignment, e.g., the indicators 26a, 26b and 28a, 28b may provide attachment or gripping positions at which the pincer grips 72 are able to hold the cuff 12. In such an embodiment, the alignment may then be performed by aligning the arms relative to one another at the proper length and rotation.

Figure 9:
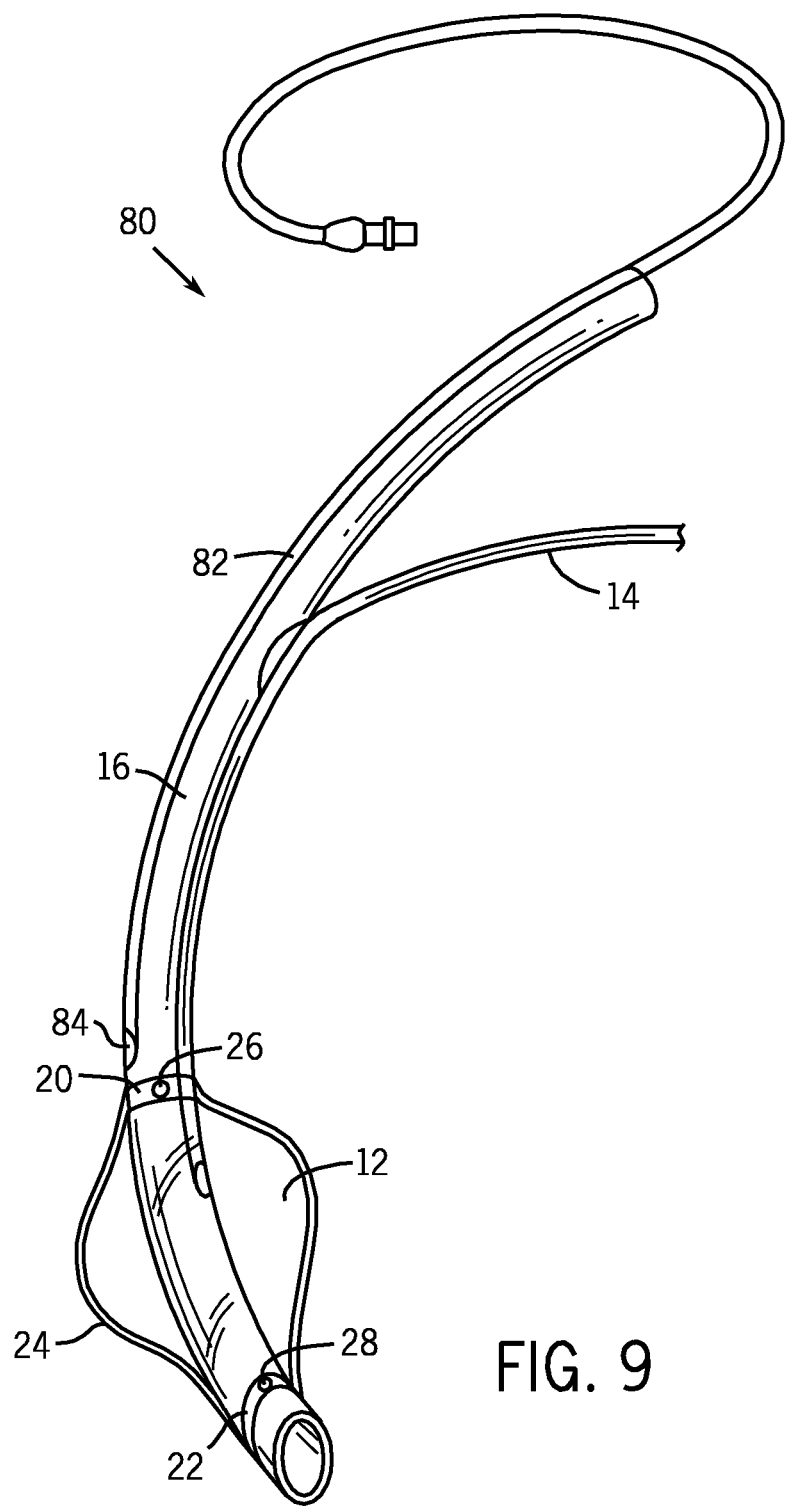
FIG. 9 illustrates an embodiment of a balloon cuff associated with a conduit adapted to suction secretions from the top of the cuff.

It is envisioned that the balloon cuffs 12 as provided may be used in conjunction with any suitable tracheal tube. FIG. 9 illustrates an embodiment of a balloon cuff associated with a tracheal tube 80 that is adapted to suction secretions from the top of the cuff. The endotracheal tube 80 includes a secretion lumen 82 that has a hole 84 located above ("proximal to") the proximal shoulder of cuff 12. The proximal collar 20 may be sealed to the tube 16 in a manner designed to move the hole 84 relative to the proximal collar 20 of the cuff 12 to facilitate aspiration of secretions that build up on this shoulder region, which may act like a shelf. While certain cuffs 12 may be aligned in an inflated state, and then adhered the tube 16, cuffs 12 for use with such a secretion lumen may also be aligned in an uninflated state, as described herein, prior to applying the specialized seal of the proximal collar region 20 to the tube 16. For example, the proximal collar region 20 may be shortened, either by initial design or by folding the collar region itself or the cuff wall material to decrease the distance between the cuff 12 and hole 84.

Figure 10:
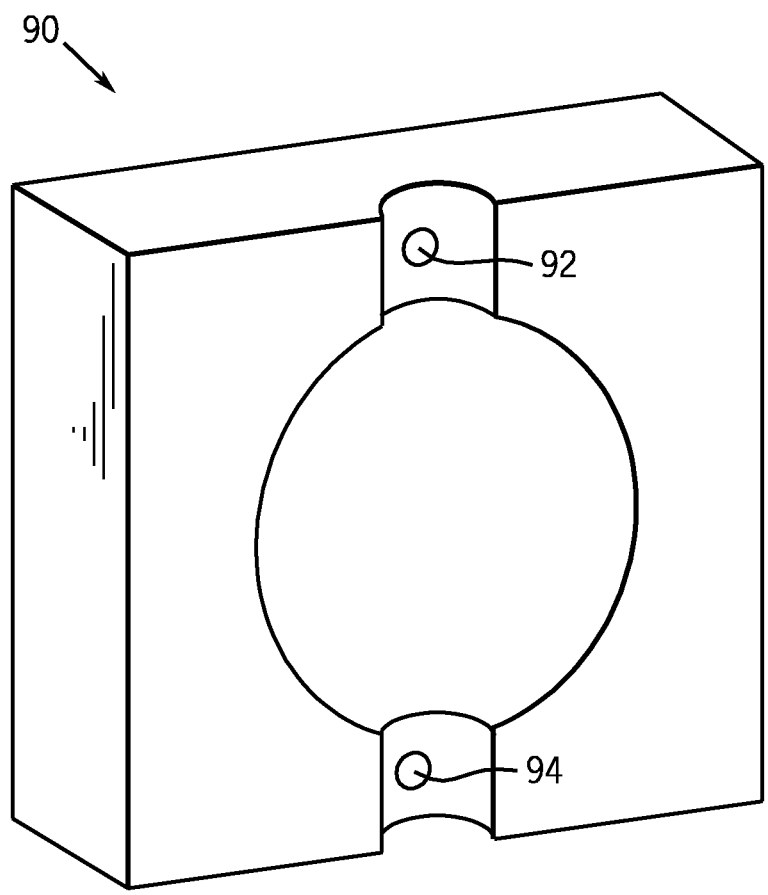
FIG. 10 depicts an exemplary mold for forming protrusions on the balloon cuff.

The cuffs 12 as provided may be manufactured by any suitable process, such as by blow molding. In one example, a tube, such as an extruded polyurethane tube, is loaded into a blowing machine or mold assembly, such as a cross-section of a mold assembly 90, depicted in FIG. 10, that includes dowels or shapes 92 and 94 in the mold corresponding to the desired shape of the alignment indicators 26 and 28, e.g., protrusions, depressions. In an embodiment, shapes 92 and 94 may include injection orifices for the injection of colored markers or chemical tags to assist in visualization of the alignment indicators. In one embodiment, the mold assembly 90 is manufactured from beryllium copper and includes a horizontal split in the assembly 90 to allow opening and closing of the mold assembly 90. In an embodiment, the mold assembly 90 may include mating symmetrical pieces that close together. The mold assembly 90 may include integrated guide pins to prevent misalignment of the two mold halves. In one embodiment, the end-portions of an extruded tube that project out from the mold are constrained to the shape and thickness of the original extruded tube by non-heat transferrable plastic holders at the ends of the mold. In one embodiment, the blow molders are model 2219H-LP blow molding machines, available from Interface Associates, that are configured to run at 1-2 bars of gas pressure. In embodiments in which the indicators (e.g., indicators 26 or 28) may comprise shaped protrusions, the protrusions may be formed by allowing extra flash along the mold 90 parting line.

Once loaded, the mold assembly 90 is closed, and the tube is clamped at each end. The mold 90 may then be heated. The tube may be stretched and air is blown into the tube via an air conduit, such as an air hose or nozzle, connected to a source of pressurized air, such as an air pump or pre-pressurized source, to achieve a desired positive pressure within the tube and to blow out the cuff walls to the shape of the mold assembly 90. Additional heat may be applied to the tube, such as via heating elements integral to the mold assembly to set the shape of the cuff 12. As the heat is applied, the stretch of the tube is relaxed and the air pressure within the tube is increased. Once the desired temperature is reached it is maintained for an interval of time. Afterward, the temperature of the mold assembly is allowed to drop or is actively cooled. A vacuum is applied within the tube, which now includes the blown cuff, to release the tube and cuff from the mold assembly and the tube and cuff are removed from the mold assembly.

For example, in one embodiment, a commercially available extrusion of Dow Pellethane® 2363-90AE having an inner diameter of 0.239±0.005 inches (6.0706±0.127 mm) and a wall thickness of 0.015 mm±0.007 mm may be blown to form a cuff 12 suitable for use with a 7.5 mm internal diameter (ID) endotracheal tube. The extruded tube may be cooled to room temperature and, when set, inserted into the mold assembly 90 automatically or by hand. Once loaded, the mold may be fitted into a sleeve of a blow-molding machine. The sleeve may be heated, such as by a series of ten electrical cartridges surrounding the sleeve, thereby heating the mold. In this embodiment, the mold may be heated to approximately 50° C. prior to stretching or blowing the extruded tube.

An air chuck locks on to one end of the extruded tube while the other end of the extruded tube if sealed by a clamp to create an airtight seal. The extruded tube is stretched by pulling on both ends of the tube and, while stretching, nitrogen or another suitable gas or gas mixture is into the extruded tube via the air chuck to pressurize the tube to between about 1 to about 3 bars. In one embodiment, the balloon will form in the portion of the tube situated within the mold when the tube expands under pressure to make contact with the internal walls of the mold.

When the cuff is fully blown against the inner walls of the mold, the mold may be heated (such as by heating the surrounding sleeve) to between about 100° C. to about 150° C. and this temperature may be maintained for between about 10 to about 30 seconds. After the application of heat, the mold may be cooled to approximately 45° C., such as by pumping refrigerated water at approximately 13° C. around the mold, to set the cuff. A vacuum is applied to the molded extrusion and cuff, and the extrusion and cuff are removed from the mold assembly.

The indicators, e.g., protrusions, on the wall of the cuff may serve as guides for cutting each cuff 12 during the manufacturing process. For example, after the cuff 12 is formed in a blow molding apparatus, the cuff 12 may be ready to be cut out from a longer extruded tube by a laser cutting machine. The laser may be set so that when a guide is focused on the protrusions, the cut is made at an appropriate distance from a proximal indicator 26 and a distal indicator 28. By using the indicators as guides, each cuff 12 may be a more uniform length.

The cuff 12 may be applied to the tube 16, which may be, for example, an extruded PVC conduit, by any suitable process. In one embodiment, the tube 16 may be inserted onto a rotating mandrel, and an operator may insert a gluing needle under the surface of the proximal collar 20 and the distal collar 22 of the cuff 12 to dispense the glue evenly.

The tracheal cuffs of the present techniques may be incorporated into systems that facilitate positive pressure ventilation of a patient, such as a ventilator. Such systems may typically include connective tubing, a gas source, a monitor, and/or a controller. The controller may be a digital controller, a computer, an electromechanical programmable controller, or any other control system.

Typically, endotracheal cuffs are inflated within a patient's trachea such that the intra cuff pressure is approximately 20-25 cm $H_2O$. Endotracheal cuffs utilizing inflation pressures significantly greater than 25 cm $H_2O$ may be referred to as high-pressure cuffs, while cuffs that are able to effectively seal the trachea at pressures less than 30 cm $H_2O$ may be considered low-pressure cuffs. In certain embodiments, intra cuff inflation pressures of 10-30 cm $H_2O$ may be used with the medical cuffs of the present techniques.

While the disclosed embodiments may be susceptible to various modifications and alternative forms, specific embodiments have been shown by way of example in the drawings and have been described in detail herein. However, it should be understood that the disclosure is not intended to be limited to the particular forms disclosed. Rather, the disclosure is to cover all modifications, equivalents, and alternatives falling within the spirit and scope of the disclosed embodiments as defined by the following appended claims.

What is claimed is:

1. A method of manufacturing a tracheal tube comprising:
passing a conduit through a proximal collar and a distal collar in a wall of the balloon cuff; and
aligning a first indicator on the proximal collar with a second indicator on the distal collar, wherein the first indicator is disposed about only a portion of a circumference of the proximal collar that is affixed to the conduit; and wherein the second indicator is disposed about only a portion of a circumference of the distal collar that is affixed to the conduit.

2. The method of claim 1, comprising aligning the first indicator and the second indicator along a set length of the conduit.

3. The method of claim 1, wherein aligning the first indicator and the second indicator along the set length of the conduit comprises inserting a rod through the conduit, wherein the rod comprises at least one alignment marker corresponding to the first indicator or the second indicator.

4. The method of claim 3, wherein aligning the first indicator and the second indicator along the set length of the conduit comprises aligning the first indicator or the second indicator to a mark or feature on the conduit.

5. The method of claim 1, wherein the first indicator and the second indicator are not identical.

6. The method of claim 1, wherein at least one of the first indicator or the second indicator comprises a protrusion or depression.

7. The method of claim 1, wherein at least one of the first indicator or the second indicator comprises text or an image.

8. The method of claim 1, wherein the conduit comprises one or more X-ray lines that run along at least a portion of the length of the conduit and wherein aligning the first indicator and the second indicator comprises alignment with at least one of the X-ray lines.

9. A method of applying an inflatable balloon cuff to a conduit comprising:
passing a conduit through a proximal collar and a distal collar in a wall of the balloon cuff; and
aligning a first indicator on the proximal collar with a second indicator on the distal collar along a set length of the conduit, wherein the alignment is substantially along an axis extending through the first indicator and the second indicator along the length of the conduit, and the alignment comprises inserting a rod through the conduit, wherein the rod comprises at least one alignment marker corresponding to the first indicator or the second indicator.

* * * * *